(12) United States Patent
Zhao

(10) Patent No.: US 9,474,637 B2
(45) Date of Patent: Oct. 25, 2016

(54) ABSORBABLE STENT HAVING A COATING FOR CONTROLLING DEGRADATION OF THE STENT AND MAINTAINING PH NEUTRALITY

(71) Applicant: Cordis Corporation, Fremont, CA (US)

(72) Inventor: Jonathon Z. Zhao, Belle Mead, NJ (US)

(73) Assignee: Cardinal Health Switzerland 515 GmbH (CH)

( * ) Notice: Subject to any disclaimer, the term of this patent is extended or adjusted under 35 U.S.C. 154(b) by 0 days.

(21) Appl. No.: 15/069,828

(22) Filed: Mar. 14, 2016

(65) Prior Publication Data

US 2016/0262916 A1    Sep. 15, 2016

Related U.S. Application Data

(63) Continuation of application No. 12/277,556, filed on Nov. 25, 2008, now Pat. No. 9,283,304.

(51) Int. Cl.
*A61F 2/06* (2013.01)
*A61F 2/89* (2013.01)
*A61L 31/14* (2006.01)
*A61L 31/16* (2006.01)
*A61L 31/10* (2006.01)
*A61L 31/02* (2006.01)

(52) U.S. Cl.
CPC ............. *A61F 2/89* (2013.01); *A61L 31/022* (2013.01); *A61L 31/10* (2013.01); *A61L 31/148* (2013.01); *A61L 31/16* (2013.01); *A61F 2250/0067* (2013.01); *A61L 2420/00* (2013.01)

(58) Field of Classification Search
CPC . A61L 31/10; A61L 31/16; A61L 2300/416; A61F 2/82; A61F 2250/0067
See application file for complete search history.

*Primary Examiner* — Thomas J Sweet
*Assistant Examiner* — Tiffany Shipmon

(57) ABSTRACT

A biocompatible metallic material may be configured into any number of implantable medical devices, including intraluminal stents. The biocompatible metallic material may comprise a magnesium alloy. The magnesium alloy implantable medical device may be designed to degrade over a given period of time. In order to control the degradation time, the device may be coated or otherwise have affixed thereto one or more coatings, one of which comprises a material for controlling the degradation time and maintain a pH neutral environment proximate the device. Additionally, therapeutic agents may be incorporated into one or more of the coatings on the implantable medical device.

2 Claims, 2 Drawing Sheets

US 9,474,637 B2

ABSORBABLE STENT HAVING A COATING FOR CONTROLLING DEGRADATION OF THE STENT AND MAINTAINING PH NEUTRALITY

BACKGROUND OF THE INVENTION

1. Field of the Invention

The present invention relates to implantable medical devices, and more particularly to absorbable metallic stents comprising a coating for sustained release of agents to control the degradation rate and to maintain pH neutrality during stent degradation.

2. Discussion of the Related Art

The purpose of many endoprostheses is to implement a support function in the interior of a lumen of the body of a patient. Accordingly, endoprostheses are designed to be implantable and have a carrier scaffold which ensures the support function. Implants of metallic materials are known. The choice of metals as the material for the carrier or scaffold structure of an implant of that nature is based in particular on the mechanical properties of metals.

In some cases, particularly in the case of such intraluminal endoprostheses as stents, a long term, durable support function afforded by the endoprosthesis is not required. Rather, in some of those situations of use, the body tissue can recover in the presence of the support prosthesis in such a way that there is no need for an ongoing supporting action by the prosthesis after a given time. That has led to the idea of making such prostheses from bioresorbable materials.

In particular, there are numerous metallic stents that are known in the art. One of the main areas of use of such stents is permanently dilating and holding open vessel constrictions, in particular, constrictions (stenoses) of the coronary vessels. In addition, aneurysm stents are also known, which afford a support function for a damaged vessel wall. Stents of that kind generally have a peripheral wall of sufficient carrying strength to hold the constricted vessel open to the desired amount. In order to permit an unimpeded flow of blood through the stent it is open at both ends. The supporting peripheral wall is generally formed by a lattice like carrier or scaffold structure which makes it possible for the stent to be introduced in a compressed condition when it is of small outside diameter to the constriction to be treated in the respective vessel and there expanded for example by means of a balloon catheter to such a degree that the vessel in the presence of the stent, after removal of the balloon catheter, is of the desired enlarged inside diameter. Basically, therefore the stent is subject to the requirement that its carrier or scaffold structure in the expanded condition affords a sufficient carrying strength to hold the vessel open. In order to avoid unnecessary vessel damage it is also desirable that, after expansion and after removal of the balloon, the stent only slightly elastically springs back (recoil) in order to have to expand the stent upon expansion thereof only as little as possible beyond the desired final diameter. Further criteria which are desirable in relation to a stent are, for example, uniform surface coverage, a structure which allows a certain degree of flexibility in relation to the longitudinal axis of the stent, and the like.

Besides the desired mechanical properties of a stent, as far as possible it should interact with the body tissue at the implantation location in such a way that renewed vessel constrictions do not occur, in particular vessel constrictions caused by the stent itself. Restenosis (re-constriction of the vessel) should be avoided as much as possible. It is also desirable if the stent is as far as possible responsible for no or only a very slight inflammatory effect. In regard to a biodegradable metal stent it is moreover desirable that the decomposition products of the metal stent as far as possible have little negative physiological effects and if possible even positive physiological effects.

A potential drawback with magnesium and magnesium alloy stents is that the magnesium and/or magnesium alloy tends to degrade rapidly in vivo and it is somewhat difficult to adjust its composition to significantly alter the degradation time. In addition, the rise in the local pH level tends to further accelerate the corrosion rate and create a burden on the surrounding tissue.

SUMMARY OF THE INVENTION

The present invention overcomes the limitations associated with magnesium alloy stents as briefly described above.

In accordance with one aspect, the present invention is directed to an intraluminal medical device. The intraluminal medical device comprising a scaffold structure formed from a biodegradable metallic material; and at least one coating affixed to the scaffold structure, the at least one coating comprising of a blend of a polylactide having a molecular weight of at least one hundred kilodaltons and a polylactide having a molecular weight of less than ten kilodaltons, the weight ratio of high molecular weight polylactide to low molecular weight polylactide is in the range from about 5:1 to about 1:5.

In accordance with another aspect, the present invention is directed to an intraluminal medical device. The intraluminal medical device comprising a scaffold structure formed from a biodegradable metallic material; and at least one coating affixed to the scaffold structure, the at least one coating comprising of a blend of a polylactide-co-glycolide having a molecular weight of at least one hundred kilodaltons and a polylactide-co-glycolide having a molecular weight of less than ten kilodaltons, the weight ratio of the high molecular weight polylactide-co-glycolide to the low molecular weight polylactide-co-glycolide is in the range from about 5:1 to about 1:5.

In accordance with another aspect, the present invention is directed to an intraluminal medical device. The intraluminal medical device comprising a scaffold structure formed from a biodegradable metallic material; and at least one coating affixed to the scaffold structure, the at least one coating comprising of a blend of a polycaprolactine having a molecular weight of at least one hundred kilodaltons and a polylactide-co-glycolide having a molecular weight of less than ten kilodaltons, the weight ratio of polycaprolactone to polylactide-co-glycolide is in the range from about 5:1 to about 1:5.

In accordance with another aspect, the present invention is directed to an intraluminal medical device. The intraluminal medical device comprising a scaffold structure formed from a biodegradable metallic material; and a polylactide having a molecular weight of at least one hundred kilodaltons and a polylactide having a molecular weight of less than ten kilodaltons and carbonyl end groups, the weight ratio of high molecular weight polylactide to low molecular weight polylactide having carboxyl end groups is in the range from about 5:1 to about 1:5.

In accordance with another aspect, the present invention is directed to an intraluminal medical device. The intraluminal medical device comprising a scaffold structure formed from a biodegradable metallic material; and a polylactide-co-glycolide having a molecular weight of at least one hundred kilodaltons and a polylactide-co-glycolide having a molecular weight of less than ten kilodaltons and carboxyl end groups, the weight ratio of high molecular weight polylactide-co-glycolide to low molecular weight polylactide-co-glycolide with carboxyl end groups is in the range from about 5:1 to about 1:5.

In accordance with another aspect, the present invention is directed to an intraluminal medical device. The intraluminal medical device comprising a scaffold structure formed from a biodegradable metallic material; and a polycaprolactone having a molecular weight of at least one hundred kilodaltons and a polylactide-co-glycolide having a molecular weight of less than ten kilodaltons and carboxyl end groups, the weight ratio of polycaprolactine to polylactide-co-glycolide with carboxy end groups is in the range from about 5:1 to about 1:5.

The present invention is directed to an implantable medical device fabricated from a magnesium alloy. Magnesium alloy stents are bioabsorbable and degrade in vivo. Accordingly, in order to achieve an optimal design, the stent is preferably coated with a material that ensures that the stent will degrade over a given controlled time period, and one that neutralizes any potential negative effects caused by the degradation of the magnesium alloy, for example a substantially neutral pH in proximity to the stent. Magnesium alloys tend to degrade in vivo and create an alkaline environment; therefore, an acid generating coating configured to provide free acid or acid end-group over a given period of time would tend to neutralize the alkaline degradation products of the magnesium alloy. The coating as stated above, would also physically tend to control the degradation of the stent. Accordingly, the synergistic combination of an acid generating polymer and the base generating stent constitute a self regulating mechanism to ensure that the stent retains its mechanical strength for a desired time; namely, a time sufficient to ensure vascular remodeling. In addition, if a therapeutic agent is affixed to the stent, the coating may create a more favorable environment for both the prolonged active life of the agent and for control over its elution rate.

BRIEF DESCRIPTION OF THE DRAWINGS

The foregoing and other features and advantages of the invention will be apparent from the following more particular description of preferred embodiments of the invention, as illustrated in the accompanying drawings.

DETAILED DESCRIPTION OF THE PREFERRED EMBODIMENTS

Figure 1:
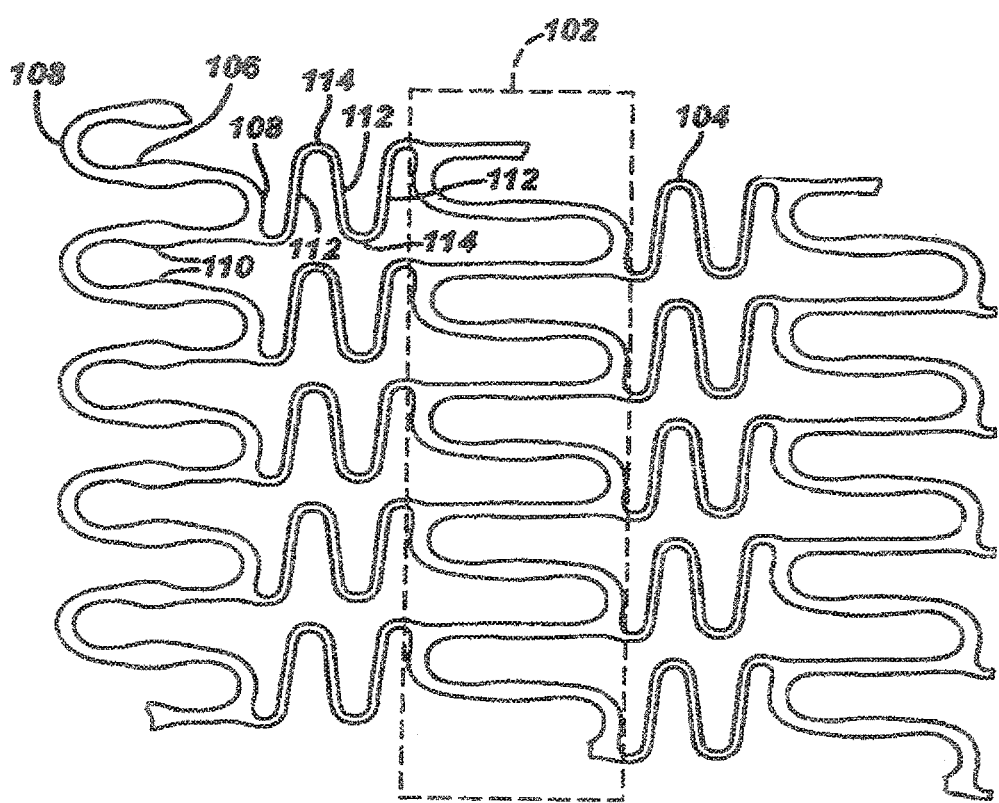
FIG. 1 is a planar representation of a portion of an exemplary stent fabricated from biocompatible materials in accordance with the present invention.

Biocompatible, solid-solution strengthened alloys such as iron-based alloys, cobalt-based alloys and titanium-based alloys as well as refractory metals and refractory-based alloys may be utilized in the manufacture of any number of implantable medical devices. The biocompatible alloy for implantable medical devices in accordance with the present invention offers a number of advantages over currently utilized medical grade alloys. The advantages include the ability to engineer the underlying microstructure in order to sufficiently perform as intended by the designer without the limitations of currently utilized materials and manufacturing methodologies.

For reference, a traditional stainless steel alloy such as 316L (i.e. UNS S31603) which is broadly utilized as an implantable, biocompatible device material may comprise chromium (Cr) in the range from about sixteen to eighteen weight percent, nickel (Ni) in the range from about ten to fourteen weight percent, molybdenum (Mo) in the range from about two to three weight percent, manganese (Mn) in the range up to two weight percent, silicon (Si) in the range up to one weight percent, with iron (Fe) comprising the balance (approximately sixty-five weight percent) of the composition.

Additionally, a traditional cobalt-based alloy such as L605 (i.e. UNS R30605) which is also broadly utilized as an implantable, biocompatible device material may comprise chromium (Cr) in the range from about nineteen to twenty-one weight percent, tungsten (W) in the range from about fourteen to sixteen weight percent, nickel (Ni) in the range from about nine to eleven weight percent, iron (Fe) in the range up to three weight percent, manganese (Mn) in the range up to two weight percent, silicon (Si) in the range up to one weight percent, with cobalt (cobalt) comprising the balance (approximately forty-nine weight percent) of the composition.

Alternately, another traditional cobalt-based alloy such as Haynes 188 (i.e. UNS R30188) which is also broadly utilized as an implantable, biocompatible device material may comprise nickel (Ni) in the range from about twenty to twenty-four weight percent, chromium (Cr) in the range from about twenty-one to twenty-three weight percent, tungsten (W) in the range from about thirteen to fifteen weight percent, iron (Fe) in the range up to three weight percent, manganese (Mn) in the range up to one and one quarter weight percent, silicon (Si) in the range from about two tenths to five tenths weight percent, lanthanum (La) in the range from about two hundredths to twelve hundredths weight percent, boron (B) in the range up to fifteen thousandths weight percent with cobalt (Co) comprising the balance (approximately thirty-eight weight percent) of the composition.

In general, elemental additions such as chromium (Cr), nickel (Ni), tungsten (W), manganese (Mn), silicon (Si) and molybdenum (Mo) were added to iron- and/or cobalt-based alloys, where appropriate, to increase or enable desirable performance attributes, including strength, machinability and corrosion resistance within clinically relevant usage conditions.

Referring to FIG. 1, there is illustrated a partial planar view of an exemplary stent 100 in accordance with the present invention. The exemplary stent 100 comprises a plurality of hoop components 102 interconnected by a plurality of flexible connectors 104. The hoop components 102 are formed as a continuous series of substantially circumferentially oriented radial strut members 106 and alternating radial arc members 108. Although shown in planar view, the hoop components 102 are essentially ring members that are linked together by the flexible connectors 104 to form a substantially tubular stent structure. The combination of radial strut members 106 and alternating radial arc members 108 form a substantially sinusoidal pattern. Although the hoop components 102 may be designed with any number of design features and assume any number of configurations, in the exemplary embodiment, the radial strut members 106 are wider in their central regions 110. This design feature may be utilized for a number of purposes, including, increased surface area for drug delivery.

The flexible connectors 104 are formed from a continuous series of substantially longitudinally oriented flexible strut members 112 and alternating flexible arc members 114. The flexible connectors 104, as described above, connect adjacent hoop components 102 together. In this exemplary embodiment, the flexible connectors 104 have a substantially N-shape with one end being connected to a radial arc member on one hoop component and the other end being connected to a radial arc member on an adjacent hoop component. As with the hoop components 102, the flexible connectors 104 may comprise any number of design features and any number of configurations. In the exemplary embodiment, the ends of the flexible connectors 104 are connected to different portions of the radial arc members of adjacent hoop components for ease of nesting during crimping of the stent. It is interesting to note that with this exemplary configuration, the radial arcs on adjacent hoop components are slightly out of phase, while the radial arcs on every other hoop component are substantially in phase. In addition, it is important to note that not every radial arc on each hoop component need be connected to every radial arc on the adjacent hoop component.

It is important to note that any number of designs may be utilized for the flexible connectors or connectors in an intraluminal scaffold or stent. For example, in the design described above, the connector comprises two elements, substantially longitudinally oriented strut members and flexible arc members. In alternate designs, however, the connectors may comprise only a substantially longitudinally oriented strut member and no flexible arc member or a flexible arc connector and no substantially longitudinally oriented strut member.

The substantially tubular structure of the stent 100 provides the scaffolding for maintaining the patentcy of substantially tubular organs, such as arteries. The stent 100 comprises a luminal surface and an abluminal surface. The distance between the two surfaces defines the wall thickness as is described in detail above. The stent 100 has an unexpanded diameter for delivery and an expanded diameter, which roughly corresponds to the normal diameter of the organ into which it is delivered. As tubular organs such as arteries may vary in diameter, different size stents having different sets of unexpanded and expanded diameters may be designed without departing from the spirit of the present invention. As described herein, the stent 100 may be formed form any number of metallic materials, including cobalt-based alloys, iron-based alloys, titanium-based alloys, refractory-based alloys and refractory metals. In addition, the stent 100 may be formed from a magnesium based alloy as briefly described below.

The carrier structure of the stent 100 illustrated in FIG. 1 comprises a magnesium alloy whose magnesium proportion is greater than ninety percent. In addition the magnesium alloy contains yttrium in a proportion of between four percent and five percent and neodymium as a rare earth element in a proportion of between one and one half percent and four percent. The remaining constituents of the alloy are less than one percent and are formed for the major part by lithium or zirconium.

This composition is based on the realization that an endoprosthesis which entirely or partially consists of the specified magnesium alloy satisfies many of the requirements involved in a quite particular positive fashion, in regard to the many different desirable properties briefly described above. Besides the mechanical requirements, a material often entirely or partially consisting of the specified magnesium alloy also satisfies the further physiological properties, that is to say a slight inflammatory effect and sustained prevention of tissue growth such as for example restenosis. In actual fact tests have shown that the decomposition products of the specified magnesium alloy have only few or indeed no substantial negative physiological effects. Therefore the specified magnesium alloy, among the large number of conceivable materials, represents an opportunity for degradable implantable medical devices.

Preferably the yttrium proportion of the magnesium alloy is between four percent and five percent. The proportion of rare earths in the magnesium alloy is preferably between one and one half percent and four percent, a preferred rare earth element being neodymium. The balance proportion in the magnesium alloy of below one percent is preferably formed for the major part by zirconium and in addition possibly lithium.

By virtue of the extremely positive properties of the specified magnesium alloy the carrier structure of the endoprosthesis preferably entirely consists of the magnesium alloy.

The material of the carrier structure is preferably extruded. It has been found that processing of the material influences the physiological effect thereof. In that sense a preferred carrier structure is one which has the following physiological properties in appropriately known cell tests: in the vitality test MTS over seventy percent absorption at four hundred ninety nm in relation to smooth muscle cells (coronary endothelium cells) with one hundred percent, that is to say a cell survival rate of over seventy percent upon cultivation of the cells with an eluate of the material of the carrier structure in comparison with untreated cells. In the proliferation test with BrdU (bromodeoxyuridine) the procedure gives a proliferation inhibition effect at below twenty percent with respect to untreated smooth muscle cells, that is to say under the influence of the magnesium alloy of the carrier structure the number of cells fluorescing by virtue of the absorption of BrdU is twenty percent with respect to a totality of one hundred percent in the comparative test with untreated muscle cells. While for example extruded carrier structures consisting of the magnesium alloy have those physiological properties, it has been found that a cast carrier structure does not have those properties. Therefore those physiological properties are at least in part governed by the production process and are not necessarily inherent properties of the magnesium alloy. An influencing factor is also the heat treatment of the magnesium alloy during processing to give the finished carrier structure.

Other magnesium alloy stents comprise small amounts of aluminum, manganese, zinc, lithium and rare earth metals as briefly described above. Magnesium normally corrodes very slowly in water in accordance with the equation given by

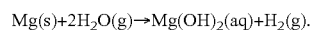

$$Mg(s)+2H_2O(g) \rightarrow Mg(OH)_2(aq)+H_2(g).$$

The other elements, particularly aluminum may degrade at a much higher rate and leach out soluble electrolytes that lead to an alkaline environment in the vicinity of the stent which may in turn hasten the degradation of the main metal ions and may lead to the premature loss of mechanical strength of the stent.

Although magnesium alloy stents offer a number of advantages, there may be a number of potential drawbacks. For example, the magnesium alloy may degrade too rapidly in vivo and it is difficult to adjust the alloy's metallic composition to change the rate of degradation. In addition, the rise of the pH in the vicinity of the stent will further accelerate the corrosion rate and create a burden on the surrounding tissue. These potential problems may be overcome by the addition of a specialized coating or coating matrix on the stent. This counter balancing force may be in the form of acid generation from the degradation of the specialized coating or coating matrix.

The degradation products associated with magnesium alloys in vivo may include hydrogen gas, aluminum hydroxide, magnesium hydroxide and other combination products. A number of these degradation products are of an alkaline nature and cause the localized pH to increase into the alkaline range. Such a buildup of the local pH subsequently hastens the degradation rate of the scaffold structure or stent body. The current generation of absorbable magnesium alloy stents lose approximately one half of their structure in about one to two months time post implantation and shows almost complete in vivo resorption within about two to six months. With the onset of the resorption process substantially coinciding with implantation of the device, the stent may quickly lose its mechanical strength. As stated above, due to the limitation of the metallurgical process in the production of absorbable magnesium alloy stents, the composition of the magnesium alloys cannot be easily changed to produce uniform magnesium alloys that have a resorption time significantly longer than two months that is preferable in stents as a platform for treating restenosis or vulnerable plaque.

In addition to the potential premature loss of mechanical strength, the increase in the localized pH as a result of the material degradation becomes detrimental to the use of certain drugs utilized in a drug/polymer matrix utilized in drug eluting stents. For example, sirolimus, a rapamycin, degrades at a relatively faster rate in an elevated pH or alkaline condition than in an acid or neutral pH condition. Accordingly, there exists a need to retard the rise in the local pH, albeit a slight rise.

In accordance with the present invention, a high molecular weight acid generating polymer may be utilized as a coating on the stent or other implantable medical device as a barrier to both prevent the diffusion of water/moisture from making contact with the absorbable magnesium alloy stent thereby delaying the onset of stent degradation after implantation while providing additional stability for any drugs affixed thereto. By varying the molecular weight and the thickness of such an acid generating polymer barrier, the onset of device degradation may be significantly delayed to offer a longer residence time to optimally treat restenosis after interventional procedures such as percutaneous transluminal coronary angioplasty. The delayed onset of stent degradation may additionally allow a significant amount of the drug affixed to the device, for example, greater than thirty percent, to be released in active forms in the critical initial period of stent implantation.

Additionally, the degradation of the acid generating polymer coating will eventually occur and generate acid end groups in the polymer chain. Such acid generation as a result of the polymer degradation may neutralize the effects of the increase in the local pH from the degradation of the stent itself. This additional self neutralization process provides a further mechanism to simultaneously slow down the degradation of the stent and maintain a superior pH environment for the unreleased drug affixed to the stent.

A polymer blend is part of a class of new materials in which two or more polymers or copolymers are blended together to create a new material with different physical properties. Essentially, the blending of polymers or copolymers provides a means of producing new materials which combine the useful properties of the constituents comprising the blend.

Alternatively, a blend of acid generating polymers or copolymers with different molecular weights may be used as a coating to provide optimized ability for the coating to generate acid end-groups during the initial period after the implantation of the device. The degradation rate of a bioabsorbable polymer is inversely proportional to its molecular weight. That is, a polymer of higher Molecular weight takes longer time to degrade. Conversely, a polymer of lower molecular weight takes a shorter time to degrade. Accordingly, a polymer or copolymer will degrade more rapidly after implantation to provide acid end-groups. Also given the same weight, a polymer or copolymer of lower Molecular weight has more polymer chains and consequently more acid end groups to be generated after polymer degradation. By blending the acid generating polymers or copolymers with different molecular weights, one can exploit the advantages of both rapid and slow degradation. In addition, this arrangement will provide more acid end groups from the beginning. This blend approach will provide a steady and larger supply of acid end-groups in the local environment to help neutralize any rise of pH as a result of the degradation of the underlying degradable metal alloy. A good blend of high and low Molecular weight polymer system is PLA or PDLA homopolymer system. A blend of PLGA with high and low Molecular weight is also suitable for this purpose.

In addition, special PLA and PLGA copolymers with acid end groups may be used for this purpose as well. The acid end group containing PLA and PLGA may be synthesized by using water or carboxylic acid as initiators for the ring opening polymerization of lactide and mixture of lactide and glycolide.

Alternatively, polymers or copolymers with acid side chains may be used as coating to provide acidic environment to help lower local pH as the degradable metallic alloys degrade after implantation. Star or dendritic shaped degradable polymers and copolymers may also be used as the coating and provide acid end groups during the degradation. For example, PLA and PLGA initiated with pentaerythritol have four arms of PLA and PLGA in the final polymers. Consequently these polymers will have four times the ability to generate acid end-groups during their degradation processes.

In accordance with one exemplary embodiment, the blend of polymers and/or copolymers comprises a high molecular weight polylactide, for example, at least one hundred kilodaltons, and a lower molecular weight polylactide, for example, less than ten kilodaltons. In this exemplary embodiment, the weight ratio of high molecular weight polylactide to low molecular weight polylactide may be in the range from about 5:1 to about 1:5.

In accordance with another exemplary embodiment, the blend of polymers and/or copolymers comprises a high molecular weight polylactide-co-glycolide, for example, at least one hundred kilodaltons, and a lower molecular weight polylactide-co-glycolide, for example, less than ten kilodaltons. In this exemplary embodiment, the weight ratio of high molecular weight polylactide-co-glycolide to low molecular weight polylactide-co-glycolide may be in the range from about 5:1 to about 1:5.

In accordance with another exemplary embodiment, the blend of polymers and/or copolymers comprises a high molecular weight polycaprolactone, for example, at least one hundred kilodaltons, and a lower molecular weight polylactide-co-glycolide, for example, less than ten kilodaltons. In this exemplary embodiment, the weight ratio of high molecular weight polycaprolactone to low molecular weight polylactide-co-glycolide may be in the range from about 5:1 to about 1:5.

In accordance with another exemplary embodiment, the blend of polymers and/or copolymers comprises a high molecular weight polylactide, for example, at least one hundred kilodaltons, and a lower molecular weight polylactide, for example, less than ten kilodaltons and having carboxyl end groups. In this exemplary embodiment, the weight ratio of high molecular weight polylactide to the low molecular weight polylactide having carboxyl end groups may be in the range from about 5:1 to about 1:5.

In accordance with another exemplary embodiment, the blend of polymers and/or copolymers comprises a high molecular weight polylactide-co-glycolide, for example, at least one hundred kilodaltons, and a lower molecular weight polylactide-co-glycolide, for example, less than ten kilodaltons and having carboxyl end groups. In this exemplary embodiment, the weight ratio of high molecular weight polylactide-co-glycolide to the low molecular weight polylactide-co-glycolide having carboxyl end groups may be in the range from about 5:1 to about 1:5.

In accordance with another exemplary embodiment, the blend of polymers and/or copolymers comprise a high molecular weight polycaprolactone, for example, at least one hundred kilodaltons and a lower molecular weight polylactide-co-glycolide, for example, less than ten kilodaltons and having carboxyl end groups. In this exemplary embodiment, the weight ratio of high molecular weight polycaprolactone to the lower molecular weight polylactide-co-glycolide having carboxyl end groups may be in the range from about 5:1 to about 1:5.

In each of the above described exemplary embodiments, the weight ratio of each constituent of the blend may be manipulated to achieve the desired mechanical and chemical properties for the blend. Specifically, the lower molecular weight constituents as will as those having carboxyl end groups control the amount of acid available during degradation, while the higher molecular weight constituents control the mechanical properties of the blend.

Figure 3:
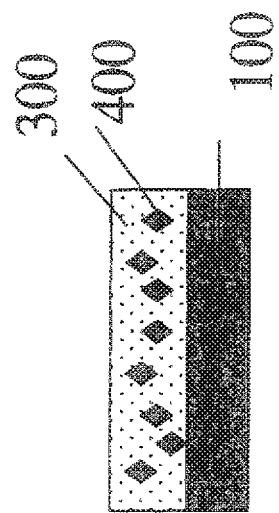
FIG. 3 is a diagrammatic representation of a component of a second exemplary stent in accordance with the present invention.
Figure 2:
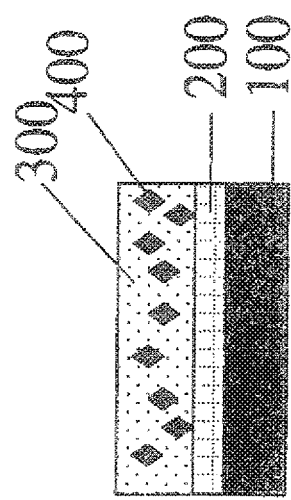
FIG. 2 is a diagrammatic representation of a component of a first exemplary stent in accordance with the present invention.

Such additional high molecular weight acid generating polymer may be used as a separating barrier between the stent and the drug containing polymer matrix as illustrated in FIG. 2 or it may serve as the drug containing coating matrix itself, as illustrated in FIG. 3. Common acid generating polymers include poly(omega-, alpha- or beta-hydroxl aliphatic acid) such as polylactide (PLA), polyglycolide (PGA), polycaprolactone (PCL), poly(trimethyl carbonate), and their myriad copolymers. Each of these polymers may be tailored for specific applications and specific drugs to provide an optimal coating scheme.

FIG. 2 illustrates the three layer configuration. The stent 100 is first coated with any of the high molecular weight acid generating polymers 200 described herein or any other suitable acid generating polymer and then coated with a polymer/drug combination layer. These polymers include PLA, PLGA, PCL, poly(ester amide). FIG. 3 illustrates a two layer configuration, wherein the stent 100 is coated with a single layer 300. This single layer 300 comprises the drug or drugs in combination with the high molecular weight acid generating polymers described above. Alternately, a combination of polymers may be utilized to form the single layer.

The local delivery of therapeutic agent/therapeutic agent combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, dips, vascular implants, tissue adhesives and sealants, tissue scaffolds, various types of dressings, bone substitutes, intraluminal devices, and vascular supports could also provide enhanced patient benefit using this drug-device combination approach. Perivascular wraps may be particularly advantageous, alone or in combination with other medical devices. The perivascular wraps may supply additional drugs to a treatment site. Essentially, any other type of medical device may be coated in some fashion with a drug or drug combination, which enhances treatment over use of the singular use of the device or pharmaceutical agent.

In addition to various medical devices, the coatings on these devices may be used to deliver therapeutic and pharmaceutic agents including: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracydclines, mitoxantrone, bleomycins, plicamycin (mithramycin) and mitomycin, enzymes (L-asparaginase which systemically metabolizes L-asparagine and deprives cells which do not have the capacity to synthesize their own asparagines); antiplatelet agents such as $G(GP) II_b/III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine and cytarabine) purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory; such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen;

indole and indene acetic acids (indomethacin, sulindac, and etodalec), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors, antisense oligionudeotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

In accordance with another exemplary embodiment, the stents described herein, whether constructed from metals or polymers, may be utilized as therapeutic agents or drug delivery devices. The metallic stents may be coated with a biostable or bioabsorbable polymer or combinations thereof with the therapeutic agents incorporated therein. Typical material properties for coatings include flexibility, ductility, tackiness, durability, adhesion and cohesion. Biostable and bioabsorbable polymers that exhibit these desired properties include methacrylates, polyurethanes, silicones, polyvinylacetates, polyvinylalcohol, ethylenevinylalcohol, polyvinylidene fluoride, poly-lactic acid, poly-glycolic acid, polycaprolactone, polytrimethylene carbonate, polydioxanone, polyorthoester, polyanhydrides, polyphosphoester, polyaminoacids as well as their copolymers and blends thereof.

In addition to the incorporation of therapeutic agents, the coatings may also include other additives such as radiopaque constituents, chemical stabilizers for both the coating and/or the therapeutic agent, radioactive agents, tracing agents such as radioisotopes such as tritium (i.e. heavy water) and ferromagnetic particles, and mechanical modifiers such as ceramic micro spheres as will be described in greater detail subsequently. Alternatively, entrapped gaps may be created between the surface of the device and the coating and/or within the coating itself. Examples of these gaps include air as well as other gases and the absence of matter (i.e. vacuum environment). These entrapped gaps may be created utilizing any number of known techniques such as the injection of microencapsulated gaseous matter.

As described above, different drugs may be utilized as therapeutic agents, including sirolimus, heparin, everolimus, pimecrolimus, tacrolimus, paditaxel, cladribine as well as classes of drugs such as statins. These drugs and/or agents may be hydrophilic, hydrophobic, lipophilic and/or lipophobic. The type of agent will play a role in determining the type of polymer. The amount of the drug in the coating may be varied depending on a number of factors including, the storage capacity of the coating, the drug, the concentration of the drug, the elution rate of the drug as well as a number of additional factors. The amount of drug may vary from substantially zero percent to substantially one hundred percent. Typical ranges may be from about less than one percent to about forty percent or higher. Drug distribution in the coating may be varied. The one or more drugs may be distributed in a single layer, multiple layers, single layer with a diffusion barrier or any combination thereof.

Different solvents may be used to dissolve the drug/polymer blend to prepare the coating formulations. Some of the solvents may be good or poor solvents based on the desired drug elution profile, drug morphology and drug stability.

There are several ways to coat the stents that are disclosed in the prior art. Some of the commonly used methods include spray coating; dip coating; electrostatic coating; fluidized bed coating; and supercritical fluid coatings.

Some of the processes and modifications described herein that may be used will eliminate the need for polymer to hold the drug on the stent. Stent surfaces may be modified to increase the surface area in order to increase drug content and tissue-device interactions. Nanotechnology may be applied to create self-assembled nanomaterials that can contain tissue specific drug containing nanoparticles. Microstructures may be formed on surfaces by microetching in which these nanoparticles may be incorporated. The microstructures may be formed by methods such as laser micromachining, lithography, chemical vapor deposition and chemical etching. Microstructures have also been fabricated on polymers and metals by leveraging the evolution of micro electro-mechanical systems (MEMS) and microfluidics. Examples of nanomaterials include carbon nanotubes and nanopartides formed by sol-gel technology. Therapeutic agents may be chemically or physically attached or deposited directly on these surfaces. Combination of these surface modifications may allow drug release at a desired rate. A top-coat of a polymer may be applied to control the initial burst due to immediate exposure of drug in the absence of polymer coating.

As described above, polymer stents may contain therapeutic agents as a coating, e.g. a surface modification. Alternatively, the therapeutic agents may be incorporated into the stent structure, e.g. a bulk modification that may not require a coating. For stents prepared from biostable and/or bioabsorbable polymers, the coating, if used, could be either biostable or bioabsorbable. However, as stated above, no coating may be necessary because the device itself is fabricated from a delivery depot. This embodiment offers a number of advantages. For example, higher concentrations of the therapeutic agent or agents may be achievable. In addition, with higher concentrations of therapeutic agent or agents, regional delivery is achievable for greater durations of time.

In yet another alternate embodiment, the intentional incorporation of ceramics and/or glasses into the base material may be utilized in order to modify its physical properties. Typically, the intentional incorporation of ceramics and/or glasses would be into polymeric materials for use in medical applications. Examples of biostable and/or bioabsorbable ceramics or/or glasses include hydroxyapatite, tricalcium phosphate, magnesia, alumina, zirconia, yittrium tetragonal polycrystalline zirconia, amorphous silicon, amorphous calcium and amorphous phosphorous oxides. Although numerous technologies may be used, biostable glasses may be formed using industrially relevant sol-gel methods. Sol-gel technology is a solution process for fabricating ceramic and glass hybrids. Typically, the sol-gel process involves the transition of a system from a mostly colloidal liquid (sol) into a gel.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed is:

1. An intraluminal medical device comprising:
   a scaffold structure formed from an amount of a biodegradable metallic material having a surface; and
   at least one coating affixed directly to the surface of the scaffold structure, the at least one coating comprising a high molecular weight acid generating polymer formed from a chemical blend of a polycaprolactone having a molecular weight of at least one hundred kilodaltons and a polylactide-co-glycolide having a molecular weight of less than ten kilodaltons, the weight ratio high molecular weight polycaprolactone to low molecular weight polylactide-co-glycolide is in the range from about 5:1 to about 1:5, wherein the high molecular weight acid generating polymer and low molecular weight acid generating polymer are configured to control degradation time of the scaffold structure and local pH level and are present in amounts selected to provide a steady supply of acidic end-groups to counter balance degradation of the amount of biodegradable metallic material of the scaffold structure.

2. The intraluminal device according to claim 1, further comprising a therapeutic agent that is released locally in therapeutically effective doses to treat a pathological condition.

* * * * *